United States Patent
Iwata et al.

(10) Patent No.: US 11,492,433 B2
(45) Date of Patent: Nov. 8, 2022

(54) HYDROGEL AND METHOD FOR PRODUCING HYDROGEL

(71) Applicants: NGK SPARK PLUG CO., LTD., Aichi (JP); NATIONAL UNIVERSITY CORPORATION HOKKAIDO UNIVERSITY, Hokkaido (JP)

(72) Inventors: Masaya Iwata, Nagoya (JP); Shinjiro Kasahara, Nagoya (JP); Jian Ping Gong, Sapporo (JP); Takayuki Kurokawa, Sapporo (JP); Takayuki Nonoyama, Sapporo (JP)

(73) Assignees: NGK SPARK PLUG CO., LTD., Aichi (JP); NATIONAL UNIVERSITY CORPORATION HOKKAIDO UNIVERSITY, Sapporo (JP)

( * ) Notice: Subject to any disclaimer, the term of this patent is extended or adjusted under 35 U.S.C. 154(b) by 183 days.

(21) Appl. No.: 16/965,868

(22) PCT Filed: Apr. 23, 2019

(86) PCT No.: PCT/JP2019/017264
§ 371 (c)(1),
(2) Date: Jul. 29, 2020

(87) PCT Pub. No.: WO2019/208576
PCT Pub. Date: Oct. 31, 2019

(65) Prior Publication Data
US 2021/0054153 A1     Feb. 25, 2021

(30) Foreign Application Priority Data
Apr. 23, 2018  (JP) .............. JP2018-082339

(51) Int. Cl.
*C08J 3/075* (2006.01)
*C08J 3/24* (2006.01)
(Continued)

(52) U.S. Cl.
CPC .......... *C08F 220/54* (2013.01); *C08F 220/56* (2013.01); *C08F 220/585* (2020.02); *C08J 3/075* (2013.01); *C08J 3/245* (2013.01)

(58) Field of Classification Search
None
See application file for complete search history.

(56) References Cited

U.S. PATENT DOCUMENTS

| 2004/0170900 A1 | 9/2004 | Sumiya et al. |
| 2005/0147685 A1* | 7/2005 | Osada ............... C08F 220/585 |
| | | 604/372 |

(Continued)

FOREIGN PATENT DOCUMENTS

| CN | 1539174 A | 10/2004 |
| JP | 3-79608 A | 4/1991 |

(Continued)

OTHER PUBLICATIONS

International Search Report (PCT/ISA/210) dated Jul. 23, 2019 by the International Searching Authority in counterpart International Patent Application No. PCT/JP2019/017264.

(Continued)

*Primary Examiner* — Joseph D Anthony
(74) *Attorney, Agent, or Firm* — Sughrue Mion, PLLC

(57) ABSTRACT

The hydrogel includes a first network structure and a second network structure. The second network structure is entwined with the first network structure. The first network structure contains a polymer crosslinked with a first crosslinking agent. The second network structure contains a polymer crosslinked with a second crosslinking agent. 50 mol % or more of the first crosslinking agent does not contain a decomposable bond. 50 mol % or more of the second crosslinking agent does not contain a decomposable bond.

8 Claims, 2 Drawing Sheets

(51) Int. Cl.
    *C08F 220/34*     (2006.01)
    *C08F 220/56*     (2006.01)
    *C08F 220/54*     (2006.01)
    *C08F 220/58*     (2006.01)

(56) References Cited

U.S. PATENT DOCUMENTS

| | | | |
|---|---|---|---|
| 2010/0029789 A1* | 2/2010 | Chen | A61P 43/00 514/777 |
| 2010/0303873 A1* | 12/2010 | Piron | A61P 17/00 514/56 |
| 2011/0184513 A1* | 7/2011 | Myung | A61F 2/142 623/5.16 |
| 2014/0142190 A1* | 5/2014 | Piron | A61P 17/16 514/738 |
| 2015/0080333 A1* | 3/2015 | Berkland | C08B 37/0072 536/53 |
| 2018/0064846 A1 | 3/2018 | Piron et al. | |
| 2019/0167844 A1 | 6/2019 | Piron et al. | |
| 2019/0358365 A1* | 11/2019 | Vaughn | A61L 27/52 |
| 2020/0407515 A1* | 12/2020 | Yamamoto | C08K 3/22 |

FOREIGN PATENT DOCUMENTS

| | | |
|---|---|---|
| JP | 2009-270032 A | 11/2009 |
| JP | 4381297 B2 | 12/2009 |
| JP | 2011-505883 A | 3/2011 |
| WO | 2009/099210 A1 | 8/2009 |
| WO | 2015/170735 A1 | 11/2015 |

OTHER PUBLICATIONS

Communication dated Oct. 26, 2021 issued by the Intellectual Property Office of the P.R.China in corresponding application No. 201980011000.2.

Communication dated Dec. 17, 2021 issued by the European Patent Office in corresponding application No. 19791497.1.

Roh, H. W., et al: "Effect of cross-link density and hydrophilicity of PU on blood compatibility of hydrophobic PS/hydrophilic PU IPNs", Journal of Biomaterials Science, Polymer Edition., vol. 10, No. 1,Jan. 1, 1999 (Jan. 1, 1999), pp. 123-143.

Rakovsky, A., et al: "Poly(ethylene glycol)-based hydrogels as cartilage substitutes: Synthesis and mechanical characteristics", Journal of Applied Polymer Science, vol. 112, No. 1, Apr. 5, 2009 (Apr. 5, 2009),pp. 390-401.

Lou X et al: "Synthesis, Physical Characterization, and Biological Performance of Sequential Homointerpenetrating Polymer Network Sponges Based onPoly(2-Hydroxyethyl Methacrylate)",Journal of Biomedical Materials Research, vol. 47, No. 3,Jan. 1, 1999 (Jan. 1, 1999), pp. 404-411.

Millar, J. R., "263. Interpenetrating Polymer Networks. Styrene-Divinylbenxene Co-polymers with Two and Three Interpenetrating Networks, and Their Sulphonates", Appl. Clzeulz, vol. 1, Jan. 1, 1960 (Jan. 1, 1960), pp. 1311-1317.

\* cited by examiner

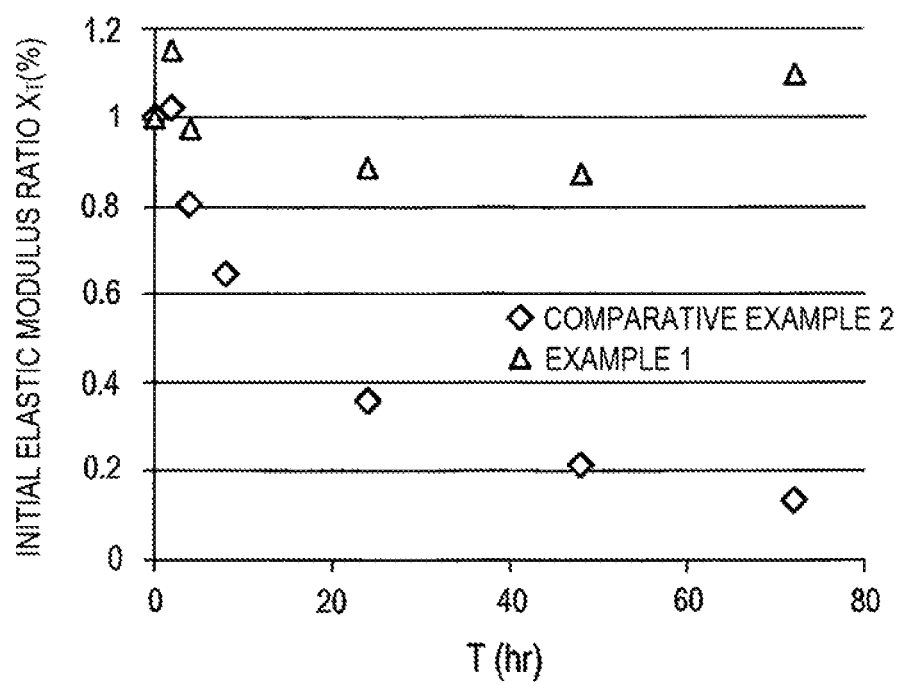

HYDROGEL AND METHOD FOR PRODUCING HYDROGEL

CROSS-REFERENCE TO RELATED APPLICATIONS

This application is a National Phase Entry of PCT International Application No. PCT/JP2019/017264 filed Apr. 23, 2019, which claims priority to Japanese Patent Application No. 2018-082339 filed Apr. 23, 2018.

TECHNICAL FIELD

The present disclosure relates to a hydrogel and a method for producing a hydrogel.

BACKGROUND ART

Conventionally, a hydrogel including a first network structure and a second network structure is known. The second network structure is entwined with the first network structure. Each of the first network structure and the second network structure is formed by polymerizing a monomer and performing a crosslinking. The hydrogel is disclosed in Patent Literature 1.

CITATION LIST

Patent Literature

Patent Literature 1: Japanese Patent No. 4381297

SUMMARY OF INVENTION

Technical Problem

In the conventional hydrogel, the elastic modulus and the strength easily decrease under acidic conditions. In one aspect of the present disclosure, it is preferable to provide a hydrogel and a method of producing a hydrogel, in which the elastic modulus and the strength are hard to decrease under acidic conditions.

Solution to Problem

In one aspect of the present disclosure, a hydrogel includes a first network structure and a second network structure intertwined with the first network structure, in which the first network structure contains a polymer crosslinked with a first crosslinking agent, the second network structure contains a polymer crosslinked with a second crosslinking agent, 50 mol % or more of the first crosslinking agent does not contain a decomposable bond, and 50 mol % or more of the second crosslinking agent does not contain a decomposable bond.

The hydrogel according to one aspect of the present disclosure is hard to be hydrolyzed at a crosslinking point under acidic conditions. Therefore, the hydrogel according to one aspect of the present disclosure is hard to decrease in elastic modulus and strength even under acidic conditions.

In another aspect of the present disclosure, a method for producing a hydrogel in which a first network structure is formed by polymerizing a first monomer and performing a crosslinking with a first crosslinking agent, a second monomer and a second crosslinking agent are introduced into the first network structure, a second network structure entwined with the first network structure is formed by polymerizing the second monomer and performing a crosslinking with the second crosslinking agent, 50 mol % or more of the first crosslinking agent does not contain a decomposable bond, and 50 mol % or more of the second crosslinking agent does not contain a decomposable bond.

The hydrogel produced by the method for producing a hydrogel according to another aspect of the present disclosure is hard to be hydrolyzed at a crosslinking point under acidic conditions. Therefore, the hydrogel produced by the method for producing a hydrogel according to another aspect of the present disclosure is hard to decrease in elastic modulus and strength even under acidic conditions.

BRIEF DESCRIPTION OF DRAWINGS

FIG. 2 is a graph showing a relationship between the initial elastic modulus ratio $X_T$ of the hydrogel and T in Example 1 and Comparative Example 2.

DESCRIPTION OF EMBODIMENTS

Figure 1:
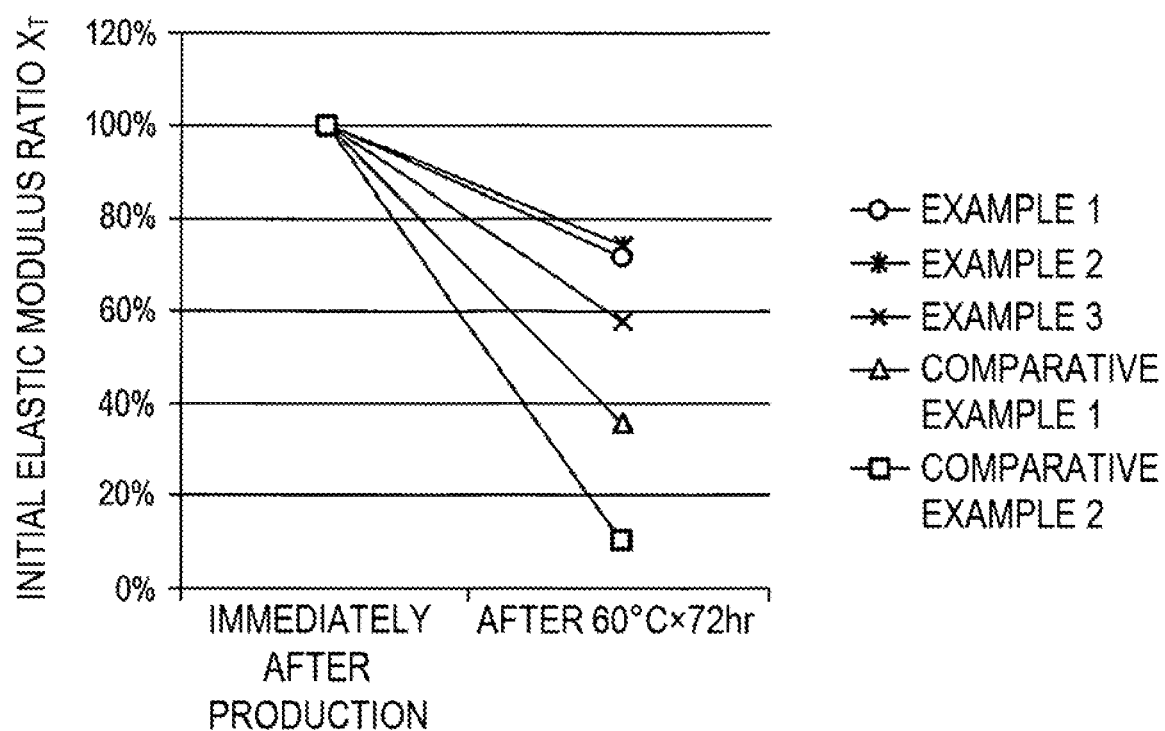
FIG. 1 is a graph showing a measurement result of an initial elastic modulus ratio $X_T$ of the hydrogel in each of Examples and Comparative Examples.

Exemplary embodiments of the present disclosure are described.

1. Hydrogel

The hydrogel of the present disclosure includes a first network structure and a second network structure. The second network structure is entwined with the first network structure.

The first network structure and the second network structure each contain a polymer formed by polymerizing a monomer. A monomer constituting the first network structure is referred to as a first monomer. A monomer constituting the second network structure is referred to as a second monomer.

Examples of the first monomer and the second monomer include monomers having an electric charge. Examples of the monomer having an electric charge include 2-acrylamido-2-methylpropanesulfonic acid, acrylic acid, methacrylic acid, and salts thereof.

Examples of the first monomer and the second monomer include electrically neutral monomers. Examples of the electrically neutral monomer include acrylamide, N,N-dimethylacrylamide, N-isopropylacrylamide, vinylpyridine, styrene, methyl methacrylate, a fluorine-containing unsaturated monomer, hydroxyethyl acrylate, vinyl acetate, and the like. Examples of the fluorine-containing unsaturated monomer include trifluoroethyl acrylate.

The first monomer and the second monomer may be different types of monomers, or may be the same type of monomers.

In the case where the first monomer and the second monomer are different types of monomers, for example, one of the first monomer and the second monomer is a monomer having an electric charge, and the other of the first monomer and the second monomer may be an electrically neutral monomer. In addition, both of the first monomer and the second monomer may be monomers having an electric charge. When both of the first monomer and the second monomer are monomers having an electric charge, different monomers may be selected from a group consisting of 2-acrylamido-2-methylpropanesulfonic acid, acrylic acid, methacrylic acid, and salts thereof. Both of the first monomer and the second monomer may be electrically neutral. When both of the first monomer and the second monomer are electrically neutral, different monomers may be selected from acrylamide, N,N-dimethylacrylamide, N-isopropylacrylamide, vinylpyridine, styrene, methyl methacrylate, the fluorine-containing unsaturated monomer, hydroxyethyl acrylate and vinyl acetate.

In the first network structure, the first monomer is polymerized to form a polymer. The first network structure is formed by crosslinking the polymer with a first crosslinking agent. 50 mol % or more of the first crosslinking agent is a crosslinking agent that does not contain a decomposable bond. As a result, hydrolysis at a crosslinking point is hard to occur even under acidic conditions. Since hydrolysis at the crosslinking point is hard to occur even under acidic conditions, the hydrogel of the present disclosure is hard to decrease in elastic modulus and strength even under acidic conditions. 60 mol % or more of the first crosslinking agent is preferably a crosslinking agent that does not contain a decomposable bond, and more preferably, 75 mol % or more of the first crosslinking agent is a crosslinking agent that does not contain a decomposable bond. The higher the ratio of the crosslinking agent without a decomposable bond of the first crosslinking agent is, the harder the elastic modulus and the strength of the hydrogel of the present disclosure is to decrease even under acidic conditions.

In the second network structure, the second monomer is polymerized to form a polymer. The polymer is crosslinked with the second crosslinking agent to form the second network structure. 50 mol % or more of the second crosslinking agent is a crosslinking agent that does not contain a decomposable bond. As a result, hydrolysis at a crosslinking point is hard to occur even under acidic conditions. Since hydrolysis at the crosslinking point is hard to occur even under acidic conditions, the hydrogel of the present disclosure is hard to decrease in elastic modulus and strength even under acidic conditions. 60 mol % or more of the second crosslinking agent is preferably a crosslinking agent that does not contain a decomposable bond, and more preferably, 75 mol % or more of the second crosslinking agent is a crosslinking agent that does not contain a decomposable bond. The higher the ratio of the crosslinking agent without a decomposable bond of the second crosslinking agent is, the harder the elastic modulus and the strength of the hydrogel of the present disclosure is to decrease even under acidic conditions. As the second crosslinking agent, the same one as the first crosslinking agent can be used.

In the first crosslinking agent and the second crosslinking agent, the decomposable bond means a bond which is easily hydrolyzed under acidic conditions. Examples of the decomposable bond include an ester bond, an amide bond, and a thioester bond. Examples of the first crosslinking agent that does not contain a decomposable bond and the second crosslinking agent that does not contain a decomposable bond each independently include divinylbenzene, divinylpyridine, divinylbiphenyl, and divinyl sulfone. All of the first crosslinking agents may be a crosslinking agent that does not contain a decomposable bond, or a part of the first crosslinking agents may be a crosslinking agent containing a decomposable bond. All of the second crosslinking agent may be a crosslinking agent that does not contain a decomposable bond, or part of the second crosslinking agent may be a crosslinking agent containing a decomposable bond. Examples of the crosslinking agent containing a decomposable bond in the first crosslinking agent and the second crosslinking agent include N,N'-methylenebisacrylamide, ethylene glycol dimethacrylate, and the like. The first crosslinking agent and the second crosslinking agent may be the same crosslinking agent or different crosslinking agents.

A main chain constituting the first network structure and a main chain constituting the second network structure preferably do not contain a decomposable bond. The main chain refers to a main chain of the polymer formed from the first monomer or a main chain of the polymer formed from the second monomer. When the main chain constituting the first network structure and the main chain constituting the second network structure do not contain a decomposable bond, hydrolysis of the main chain is hard to occur even under acidic conditions. Since hydrolysis of the main chain is hard to occur under acidic conditions, the elastic modulus and the strength of the hydrogel of the present disclosure are further hard to decrease even under acidic conditions.

In the hydrogel of the present disclosure, an initial elastic modulus ratio X defined by the following Formula (1) is preferably 50% or more.

$$X=(E2/E1)\times 100 \qquad \text{Formula (1)}$$

(in Formula (1), E2 is an elastic modulus of the hydrogel after a treatment for 72 hours in an aqueous hydrochloric acid solution having a hydrochloric acid concentration of 0.05 mol/L and a temperature of 60° C. E1 is an elastic modulus of the hydrogel before the treatment.) When the initial elastic modulus ratio X is 50% or more, the hydrogel of the present disclosure is further hard to decrease in elastic modulus and strength even under acidic conditions.

The degree of crosslinking of the first network structure is, for example, preferably in the range of 1 mol % to 50 mol %. The degree of crosslinking means a value representing the ratio of the molar concentration of the crosslinking agent to the charged molar concentration of the monomer as a percentage unit. In practice, there may be a slight amount of the monomer that is not actually involved in the polymerization or a crosslinking agent that is not involved in the crosslinking, but in this case as well, the meaning of the degree of crosslinking in the present specification is as described above. The degree of crosslinking of the second network structure is, for example, preferably in the range of 0.001 mol % to 20 mol %. When the degrees of crosslinking of the first network structure and the second network structure are within the above ranges, the hydrogel of the present disclosure has a higher mechanical strength.

It is preferable that the first network structure has a high hardness and the second network structure has a high extensibility. When the first network structure has a high hardness and the second network structure has a high extensibility, the hydrogel of the present disclosure has a higher strength.

The degree of crosslinking of the second network structure is preferably smaller than the degree of crosslinking of the first network structure. When the degree of crosslinking of the second network structure is smaller than the degree of crosslinking of the first network structure, the first network structure has a high hardness, and the second network structure has a high extensibility. As a result, the hydrogel of the present disclosure has a high strength.

A component amount of the first monomer in the hydrogel of the present disclosure is referred to as M1 (mol). A component amount of the second monomer in the hydrogel of the present disclosure is referred to as M2 (mol). The molar ratio of M1 and M2 (hereinafter, M1:M2) is preferably in the range of 1:2 to 1:100, more preferably in the range of 1:3 to 1:50, and particularly preferably in the range of 1:3 to 1:30. When M1:M2 is within the above range, the mechanical strength of the hydrogel of the present disclosure can be further improved.

The water content of the hydrogel of the present disclosure is preferably from 10% to 99.9%. The compression stress at rupture of the hydrogel of the present disclosure is preferably 1 MPa to 100 MPa. The tensile stress at rupture of the hydrogel of the present disclosure is preferably 0.1 MPa to 100 MPa.

Examples of applications of the hydrogel of the present disclosure include, for example, artificial cartilages, artificial joints, artificial organs, cell culture substrates, drug delivery systems (DDS), contact lenses, intraocular lenses, hollow fibers, carriers for drug delivery, soft actuators used for a tip of a specific substance sensor or catheter, mats for preventing bedsore and decubitus, cushions, lubricants, stabilizers or thickeners for cosmetics, fuel cell materials, battery separators, diapers, sanitary articles, sustained release agents, materials of construction, building materials, and the like. Examples of the artificial organs include artificial blood vessels and artificial skin.

2. Method for Producing Hydrogel

In a method for producing the hydrogel of the present disclosure, a first network structure is formed. The first network structure can be formed, for example, as follows. A first polymerization solution containing a first monomer, a first crosslinking agent, and a polymerization initiator is prepared. Next, the first monomer is polymerized and a crosslinking is performed with the first crosslinking agent to form the first network structure.

Next, a second network structure is formed. The second network structure can be formed, for example, as follows. A second polymerization solution containing a second monomer, a second crosslinking agent, and a polymerization initiator is prepared. Next, a gel having the first network structure is immersed in the second polymerization solution and stored in a immersed state. At this time, the second monomer and the second crosslinking agent are introduced into the first network structure to diffuse and infiltrate. Next, the gel having the first network structure is removed from the second polymerization solution. Next, the second monomer introduced into the first network structure is polymerized and a crosslinking is performed with a second crosslinking agent. As a result, a second network structure entwined with the first network structure is formed.

The first crosslinking agent and the second crosslinking agent used in the method for producing a hydrogel of the present disclosure are those described in the section of "1. Hydrogel". Therefore, the hydrogel produced by the method for producing a hydrogel of the present disclosure is hard to be hydrolyzed at a crosslinking point even under acidic conditions. As a result of being hard to be hydrolyzed at a crosslinking point even under acidic conditions, the hydrogel produced by the method for producing a hydrogel of the present disclosure is hard to decrease in elastic modulus and strength even under acidic conditions.

The polymerization initiators contained in the first polymerization solution and the second polymerization solution are not particularly limited, and can be appropriately selected depending on the type of the monomers. When the monomer is thermally polymerized, for example, a water-soluble thermal catalyst such as potassium persulfate, a redox initiator such as potassium persulfate-sodium thiosulfate, azobisisobutyronitrile (AIBN), benzoyl peroxide (BPO), or the like can be used as the polymerization initiator. When the monomer is photopolymerized, for example, 2-oxoglutaric acid, benzophenone, hydrogen peroxide solution, or the like can be used as the polymerization initiator.

Solvents in the first polymerization solution and the second polymerization solution are not particularly limited, and can be appropriately selected. Examples of the solvent include water, an organic solvent, a mixed solvent of water and an organic solvent, and the like. Examples of the organic solvent include dimethyl sulfoxide, 2-methyl-2-propanol, and tetrahydrofuran. The solvents in the first polymerization solution and the solvent in the second polymerization solution are preferably the same. When the solvent in the first polymerization solution and the solvent in the second polymerization solution are the same, the first network structure and the second network structure are more easily entwined.

Examples of the method for polymerizing the first monomer include a thermal polymerization, a photopolymerization, and the like. Examples of light used in photopolymerization include ultraviolet rays or the like. Examples of the method for crosslinking the polymer formed from the first monomer by the first crosslinking agent include a thermal crosslinking, a photocrosslinking and the like. Examples of light used in the photocrosslinking include ultraviolet rays, and the like. The polymerization of the first monomer and the crosslinking using the first crosslinking agent may be performed at the same time, or the crosslinking may be performed after the polymerization.

Examples of the method for polymerizing the second monomer include thermal polymerization, photopolymerization, and the like. Examples of light used in photopolymerization include ultraviolet rays or the like. Examples of the method for crosslinking the polymer formed from the second monomer by the second crosslinking agent include thermal crosslinking, photocrosslinking and the like. Examples of light used in the photocrosslinking include ultraviolet rays, and the like. The polymerization of the second monomer and the crosslinking of the second monomer using the second crosslinking agent may be performed at the same time, or crosslinking may be performed after polymerization.

3. Examples (3-1) Production of Hydrogel in Example 1

2-acrylamide-2-methylpropane sulfonic acid (AMPS), divinylbenzene (DVB), and 2-oxoglutaric acid were added to a mixed solvent to prepare a first polymerization solution. The concentration of 2-acrylamide-2-methylpropane sulfonic acid in the first polymerization solution was 1 mol/L. The concentration of divinylbenzene in the first polymerization solution was 0.04 moL/L. The concentration of 2-oxoglutaric acid in the first polymerization solution was 0.01 mol/L. The mixed solvent was a mixed solvent of pure water and dimethyl sulfoxide (DMSO).

The 2-acrylamide-2-methylpropane sulfonic acid corresponds to the first monomer. The divinylbenzene corresponds to the first crosslinking agent. The 2-oxoglutaric acid corresponds to the polymerization initiator.

Next, the first polymerization solution was deoxygenated using nitrogen gas. Next, the first polymerization solution was poured into a glass polymerization vessel. Next, the first polymerization solution was irradiated with ultraviolet rays using a UV lamp. The wavelength of the ultraviolet rays was 365 nm. The output of the UV lamp was 22 W. The output current of the UV lamp was 0.34 A. The ultraviolet irradiation was performed at room temperature for 8 hours. At this time, the 2-acrylamido-2-methylpropane sulfonic acid and divinylbenzene were polymerized and a crosslinking with divinylbenzene was performed to form an AMPS gel. The AMPS gel corresponds to the first network structure.

Next, N,N-dimethylacrylamide (DMAAm), divinylbenzene and 2-oxoglutaric acid were added to a mixed solvent to prepare a second polymerization solution. The concentration of N,N-dimethylacrylamide in the second polymerization solution was 2 mol/L. The concentration of divinylbenzene in the second polymerization solution was 0.002 mol/L. The concentration of 2-oxoglutaric acid in the second polymerization solution was 0.005 moL/L. The mixed solvent was a mixed solvent of pure water and dimethyl sulfoxide.

The N,N-dimethylacrylamide corresponds to the second monomer. The divinylbenzene corresponds to the second crosslinking agent. The 2-oxoglutaric acid corresponds to the polymerization initiator.

Next, the AMPS gel was immersed in the second polymerization solution. At this time, the second polymerization solution was introduced into the AMPS gel and diffused and infiltrated. Hereinafter, the AMPS gel in which the second polymerization solution is diffused and infiltrated is referred to as a diffusion/infiltration gel.

Next, the diffusion/infiltration gel was removed from the second polymerization solution and cut into an appropriate size. Next, the diffusion/infiltration gel was irradiated with ultraviolet rays using a UV lamp. The wavelength of the ultraviolet rays was 365 nm. The output of the UV lamp was 22 W. The output current of the UV lamp was 0.34 A. The ultraviolet irradiation was performed at room temperature for 8 hours. At this time, in the diffusion/infiltration gel, N,N-dimethylacrylamide and divinylbenzene, which are components of the second polymerization solution, were polymerized and a crosslinking with divinylbenzene was performed to form a second network structure. The second network structure was entwined with the first network structure. A hydrogel was obtained by the above steps. The obtained hydrogel was a double network gel in which the first network structure and the second network structure were formed independently. The obtained hydrogel was left to stand in pure water until the hydrogel arrives at an equilibrium swelling. Further, the hydrogel was washed with pure water until there is no unreacted monomer or the like in the hydrogel.

(3-2) Production of Hydrogels in Examples 2 and 3 and Comparative Examples 1 and 2

Hydrogels in Examples 2 and 3 and Comparative Examples 1 and 2 were basically produced in substantially the same manner as in Example 1. However, the first crosslinking agent and the second crosslinking agent are different from those in Example 1. The total number of moles of the first crosslinking agent and the total number of moles of the second crosslinking agent are the same in Examples 1 to 3 and Comparative Examples 1 and 2.

The first crosslinking agent and the second crosslinking agent in Example 2 each were a mixture of divinylbenzene and N,N'-methylenebisacrylamide (MBAA). N,N'-methylenebisacrylamide has an amide bond. The amide bond corresponds to the decomposable bond.

The molar ratio of divinylbenzene to N,N'-methylenebisacrylamide is hereinafter referred to as DVB/MBAA. The DVB/MBAA of the first crosslinking agent and the second crosslinking agent in Example 2 was 75/25, respectively.

The first crosslinking agent and the second crosslinking agent in Example 3 each were a mixture of divinylbenzene and N,N'-methylenebisacrylamide. The DVB/MBAA of the first crosslinking agent and the second crosslinking agent in Example 3 was 50/50, respectively.

The first crosslinking agent and the second crosslinking agent in Comparative Example 1 each were a mixture of divinylbenzene and N,N'-methylenebisacrylamide. The DVB/MBAA of the first crosslinking agent and the second crosslinking agent in Comparative Example 1 was 25/75, respectively.

The first crosslinking agent and the second crosslinking agent in Comparative Example 2 were only N,N'-methylenebisacrylamide.

In Table 1, for Examples 1 to 3 and Comparative Examples 1 and 2, a degree of crosslinking of the first network structure, a molar ratio of the crosslinking agent containing no decomposable bond in the first crosslinking agent, a degree of crosslinking of the second network structure, and a molar ratio of the crosslinking agent containing no decomposable bond to the second crosslinking agent, and M1:M2 (molar ratio) were shown.

TABLE 1

| | First Network Structure | | Second Network Structure | | |
|---|---|---|---|---|---|
| | Degree Of Crosslinking | Molar Ratio of Crosslinking Agent containing no Decomposable Bond in First Crosslinking Agent | Degree Of Crosslinking | Molar Ratio of Crosslinking Agent containing no Decomposable Bond in Second Crosslinking Agent | M1:M2 (Molar Ratio) |
| Example 1 | 4% | 100 mol % | 0.1% | 100 mol % | 1:2 |
| Example 2 | 4% | 75 mol % | 0.1% | 75 mol % | 1:2 |
| Example 3 | 4% | 50 mol % | 0.1% | 50 mol % | 1:2 |
| Comparative Example 1 | 4% | 25 mol % | 0.1% | 25 mol % | 1:2 |
| Comparative Example 2 | 4% | 0 mol % | 0.1% | 0 mol % | 1:2 |

Degree of Crosslinking: a value representing the ratio of the molar concentration of the crosslinking agent to the charged molar concentration of the monomer, as a percentage unit.
M1:M2 (molar ratio): a molar ratio of charge amounts of the first monomer and the second monomer (3-3) Production of Single Network Hydrogels in Comparative Examples 3 and 4

A single network hydrogel in Comparative Example 3 was produced using the first polymerization solution in Example 1. The single network hydrogel in Comparative Example 3 had a single network structure. In addition, a single network hydrogel in Comparative Example 4 was produced using the second polymerization solution in Example 1. The single network hydrogel in Comparative Example 4 had a single network structure.

(3-4) Compression Test

The hydrogel in Example 1 and the single network hydrogels in Comparative Examples 3 and 4 were subjected to a compression test. For the compression test, a Tensilon universal testing machine manufactured by Orientec Co., Ltd. was used. The compression test method is as follows.

A test specimen was cut out from the gel. The test specimen was clamped by a compression test jig of the testing machine and compressed at a predetermined compression speed. The compression test jig is composed of two flat plates. The compression speed was a speed at which 10% of the thickness of the test specimen was compressed in one minute. The compression stress at rupture and the compression strain at rupture were measured under the above conditions. The initial elastic modulus was calculated from the inclination of the primary linear approximation in the initial strain portion of the stress-strain curve. The measurement results of the compression stress at rupture, the compression strain at rupture, and the initial elastic modulus of the hydrogels in Example 1 and Comparative Examples 3 and 4 are shown in Table 2.

TABLE 2

|  | Example 1 | Comparative Example 3 | Comparative Example 4 |
| --- | --- | --- | --- |
| Compression Stress at Rupture (MPa) | 8.8 | 0.08 | 0.8 |
| Compression Strain at Rupture (%) | 88 | 29 | 90 |
| Initial Elastic Modulus (MPa) | 0.6 | 0.2 | 0.01 |
| Degree of Swelling (%) | 9 | 60 | 30 |

The initial elastic modulus and the compression stress at rupture of the hydrogel of Example 1 were significantly higher than those of the single network hydrogels of Comparative Examples 3 and 4. From this result, it was confirmed that the hydrogel in Example 1 was a double network gel.

(3-5) Measurement of Degree of Swelling

For the hydrogel in Example 1 and the single network hydrogels in Comparative Examples 3 and 4, the degree of swelling was obtained according to the following formula (2). The obtained degree of swelling is shown in Table 1 above.

Degree of swelling=weight of swollen gel ($WW$)/dry gel weight ($WD$)　　　Formula (2)

The hydrogel in Example 1 had a lower degree of swelling than the single network hydrogels in Comparative Examples 3 and 4.

(3-6) Deterioration Test

The hydrogels in Examples 1 to 3 and Comparative Examples 1 and 2 were subjected to a deterioration test. A method of the deterioration test is as follows.

The elastic modulus of the hydrogel is measured immediately after a production of the hydrogel. The elastic modulus at this time is defined as E1. Next, the hydrogel is immersed in an aqueous hydrochloric acid solution having a hydrochloric acid concentration of 0.05 mol/L and a pH of 1.3 at 25° C. for 24 hours. By this immersion, the aqueous hydrochloric acid solution infiltrates into the hydrogel. Next, the hydrogel is immersed in an aqueous hydrochloric acid solution having a hydrochloric acid concentration of 0.05 mol/L and a temperature of 60° C. for T hours. T is in the range of 0 to 72. The hydrogel is then removed from the aqueous hydrochloric acid solution and the elastic modulus of the hydrogel is measured. The elastic modulus at this time is defined as $E2_T$. The initial elastic modulus ratio $X_T$ (%) defined by the following formula (3) is calculated.

$X_T=(E2_T/E1)\times100$　　　Formula (3)

The measurement result of the initial elastic modulus ratio $X_T$ is shown in FIG. 1. "60° C.×72 hr" in FIG. 1 represents the initial elastic modulus ratio $X_T$ when T is 72 hours. The initial elastic modulus ratio $X_T$ when T is 72 corresponds to the initial elastic modulus ratio X.

The initial elastic modulus ratios $X_T$ of the hydrogels in Examples 1 to 3 were significantly higher than the initial elastic modulus ratios $X_T$ in the hydrogels in Comparative Examples 1 and 2.

A relationship between the initial elastic modulus ratios $X_T$ and T in the hydrogels in Example 1 and Comparative Example 2 is shown in FIG. 2. In the hydrogel in Example 1, even when T was increased, the initial elastic modulus ratio $X_T$ was hard to decrease. On the contrary, in the hydrogel in Comparative Example 2, the initial elastic modulus ratio $X_T$ significantly decreased as T increased.

4. Other Embodiments

Although the embodiments of the present disclosure have been described above, the present disclosure is not limited to the embodiments described above, and various modifications may be made.

(1) The functions of one component in each of the above-described embodiments may be shared by a plurality of components, or functions of a plurality of components may be exerted by one component. A part of the configuration of each of the above-described embodiments may be omitted. At least a part of the configuration of each of the above-described embodiments may be added to or replaced with the configuration of another embodiment. Every embodiments included in the technical idea specified from the wording described in the claims are an embodiment of the present disclosure.

(2) In addition to the hydrogels described above, the present disclosure can also be achieved in various forms such as a product containing the hydrogel as a component.

The invention claimed is:

1. A hydrogel comprising:
    a first network structure; and
    a second network structure entwined with the first network structure,
    wherein the first network structure contains a polymer crosslinked with a first crosslinking agent, the second network structure contains a polymer crosslinked with a second crosslinking agent, 50 mol % or more of the first crosslinking agent does not contain a decomposable bond, and 50 mol % or more of the second crosslinking agent does not contain a decomposable bond, and
    wherein more than 0 mol % and less than 50 mol % of the first crosslinking agent includes a decomposable bond, and more than 0 mol % and less than 50 mol % of the second crosslinking agent includes a decomposable bond.

2. The hydrogel according to claim 1, wherein the main chain constituting the first network structure and the main chain constituting the second network structure do not contain a decomposable bond.

3. The hydrogel according to claim 1, wherein
the decomposable bonds in the first crosslinking agent and the second crosslinking agent each independently contain one or more selected from an amide bond, an ester bond, and a thioester bond.

4. The hydrogel according to claim 1, wherein
the first crosslinking agent and the second crosslinking agent that contain the decomposable bond each independently contain one or more selected from a group consisting of N,N'-methylenebisacrylamide and ethylene glycol dimethacrylate.

5. The hydrogel according to claim 1, wherein
the first crosslinking agent and the second crosslinking agent that do not contain the decomposable bond each independently contain one or more selected from a group consisting of divinylbenzene, divinylpyridine, divinylbiphenyl, and divinyl sulfone.

6. The hydrogel according to claim 1, which has an initial elastic modulus ratio X of 50% or more, as defined by the following formula (1):

$$X=(E2/E1)\times 100 \qquad \text{Formula (1)}$$

in Formula (1), E2 is an elastic modulus of the hydrogel after a treatment for 72 hours in an aqueous hydrochloric acid solution having a hydrochloric acid concentration of 0.05 mol/L and a temperature of 60° C.; E1 is an elastic modulus of the hydrogel before the treatment.

7. A method for producing a hydrogel, comprising:
polymerizing a first monomer and performing a crosslinking with a first crosslinking agent to form a first network structure;
introducing a second monomer and a second crosslinking agent into the first network structure; and
polymerizing the second monomer, and performing a crosslinking with the second crosslinking agent to form a second network structure entwined with the first network structure,
wherein 50 mol % or more of the first crosslinking agent does not contain a decomposable bond, and 50 mol % or more of the second crosslinking agent does not contain a decomposable bond, and
wherein more than 0 mol % and less than 50 mol % of the first crosslinking agent includes a decomposable bond, and more than 0 mol % and less than 50 mol % of the second crosslinking agent includes a decomposable bond.

8. The method for producing a hydrogel according to claim 7, wherein
the decomposable bonds in the first crosslinking agent and the second crosslinking agent each independently contain one or more selected from a group of an amide bond, an ester bond, and a thioester bond.

* * * * *